United States Patent

Nagypal et al.

[11] Patent Number: 6,146,410
[45] Date of Patent: Nov. 14, 2000

[54] APPARATUS FOR THE PHOTODYNAMIC TREATMENT OF LIVING BEINGS OR ORGANS THEREOF

[76] Inventors: Tibor Nagypal, Schulzgasse 15/6, A-1210 Vienna; Gunther Hofmann, Cottagegasse 70, A-1190 Vienna, both of Austria

[21] Appl. No.: 09/077,066
[22] PCT Filed: Apr. 18, 1996
[86] PCT No.: PCT/AT96/00075
  § 371 Date: Dec. 17, 1998
  § 102(e) Date: Dec. 17, 1998
[87] PCT Pub. No.: WO97/19725
  PCT Pub. Date: Jun. 5, 1997

[30] Foreign Application Priority Data

Nov. 24, 1995 [AT] Austria ................................. 1930/95

[51] Int. Cl.[7] .................................................. A61B 18/18
[52] U.S. Cl. ............................... 607/88; 607/89; 606/10; 606/12; 606/13
[58] Field of Search .................................. 606/1, 2, 3, 10, 606/11, 12, 13, 14, 15, 16, 17; 607/88, 89, 90

[56] References Cited

U.S. PATENT DOCUMENTS

| 4,889,129 | 12/1989 | Doughtery et al. ..................... 606/16 |
| 5,344,434 | 9/1994 | Talmore ..................................... 606/3 |
| 5,377,676 | 1/1995 | Vari et al. ................................. 606/2 |
| 5,519,534 | 5/1996 | Smith et al. ............................. 606/16 |
| 5,616,140 | 4/1997 | Prescott ................................... 606/10 |
| 5,814,041 | 9/1998 | Anderson et al. ....................... 606/15 |

Primary Examiner—Linda C. M. Dvorak
Assistant Examiner—Bryan K. Yarnell
Attorney, Agent, or Firm—Wolf, Greenfield & Sacks, P.C.

[57] ABSTRACT

An apparatus for the photodynamic treatment of living beings or organs thereof which includes a light source, a switching device, a current source, and a computer. The light source is controllable with respect to intensity, time, wavelength, and/or spectral bands by the computer in order to obtain a predetermined spectral pattern (photon energy pattern), which is preferably a pattern sequence.

16 Claims, 9 Drawing Sheets

APPARATUS FOR THE PHOTODYNAMIC TREATMENT OF LIVING BEINGS OR ORGANS THEREOF

FIELD OF THE INVENTION

This invention relates to a device for the photodynamic treatment of living beings and of the organs thereof, for which a light source, a switching device and a power source are provided.

BACKGROUND OF THE INVENTION

The photodynamic treatment of living beings and of the organs thereof depends on the fact that biophotochemical effects are initiated in the body by specific dyes and these effects accumulate, for example, in cancerous tissues at a 10 to 30-fold concentration, referred to the healthy tissue. This can then lead to the release in the cells of such cancerous tissues of singlet oxygen, which selectively destroys the cancer cells.

In the known devices, the treatment is carried out in a way, that by the light source, the light is emitted into the tissue for an empirically determined time without a carefully directed control.

It has now been found experimentally that, during the emission of the light, the optical tissue properties and the tissue-photon interactions continually alter in different narrow spectral band ranges. The tissues contain a number of dyes which react on the photons impinging in a narrow spectral band wavelength range and this then gives rise to the biophotochemical processes. The therapeutic effect is hence totally dependent on the dye concentration, the optical properties of the diseased tissue, the light intensity applied, the spectral composition of the light and the general condition of the patient; the different wavelengths of the light as well as the light intensity are of great importance here.

SUMMARY OF THE INVENTION

The invention is based on the object of developing a device of the above-mentioned type wherein, besides the wavelength of the light or the spectral wavelength range, the light intensity is also taken into account.

This is achieved according to the invention by the feature that the light source can be controlled with respect to its intensity and/or spectral bands by means of a computer in order to obtain a given spectral pattern (photon energy pattern), preferably a sequence of patterns. It thereby becomes possible to accommodate the radiant intensity and the wavelength or the spectral structure to the respective biophotochemical processes, and at the same time a spectral pattern which is variable over time can also be emitted into the tissue.

By a spectral pattern is meant here a spectrally structured light which is variable over time and consists of one or more spectral bands. The simplest spectral pattern can be characterised by a four-dimensional vector wherein the vector coordinates are the energy of the band, the band width, the average band wavelength and the time. These four vectors are preset for the light source by an appropriate computer, the commuter being preset in accordance with the individual data.

To achieve the preset spectral pattern, the computer may advantageously be provided with an expert data bank. The computer consequently contains key features already determined on the basis of clinical practice, so that resort can be made to clinically proven spectral patterns for the treatment of certain diseases and a possibly lengthy experimentation is therefore unnecessary. To determine whether the spectral pattern emitted onto the tissue displays the desired action, the computer can be connected to sensors for the acquisition of data for the tissue being treated. The computer can be provided with a comparator to compare the data bank acquired by the sensor or sensors with that of the expert data bank, by which means it can immediately be determined whether the tissue reacts with the spectral pattern in the desired manner. The sensors can be connected to a working data bank which processes the determined data for the comparator, the working data bank being connected to the expert data bank. It is thereby possible to correct the expert data bank with respect to the data signalled back from the tissue, in order to attain an optimal effect of the device tailored to the respective individual.

In a particularly preferred construction, the sensors can be designed for the acquisition of data for the healthy tissue and can be connected to a reference data bank, with the comparator being designed to compare the desired values of the healthy tissue acquired by the sensors with the actual values or the diseased tissue.

A beam coupler can be connected in front of the light source to ensure the carefully directed introduction of the beams of light into the tissue, whereby an optimal utilisation of the radiated light is achieved. The beam coupler may have a system of lenses and/or mirrors for the purpose of alignment and/or selection of the beams of light. It is thereby possible to construct the appropriate spectral pattern specifically and to introduce the beams appropriately aligned into the tissue. To the same end, a reflecting prism or reflecting cone can be interposed in the path of the beams for the purpose of alignment and/or selection of the beams of light.

In another version of the beam coupler, an optical fibre may be provided for the alignment and/or selection of the beams of light. All this serves the purpose, already stated above, of specifically constructing the photon energy pattern. Furthermore the devices provided in the beam coupler for the alignment and/or selection of the beams of light can be adjustable relative to one another in order to define the geometry of the surface area to be irradiated, the purpose of which is to direct the radiation exclusively onto the diseased tissue and not to expose the healthy tissue to the radiation.

To achieve a carefully calculated direction of the data produced from the tissue to the sensors, sensor couplers can be connected in front of the sensors for the carefully calculated acquisition of the data from the tissue to be treated. Here the sensor couplers can be constructed similarly to the beam couplers, in order in this way to analyse the photon patterns to transmit them in suitably, processed form to the computer. Here the sensor coupler, in addition to containing the lens system and/or mirror system and/or optical fibre system, may also have electrodes and/or sensing probes for the additional determination of physical and/or physiological chemical measured data, as the biological reaction of the cells can be assessed by means of these physical and/or physiological chemical measured data.

The light source can be in the form of a wide band light source, to which a light distributor and one or more spectral band filters and/or intensity modules are connected in tandem. Consequently a single light source can be used, while the device is available for many different kinds of applications, since an adaptation is possible simply by altering the light distributor and/or the spectral band filters and/or intensity modules. Where there are several spectral band filters and/or intensity modules, each component can be separately controllable, so as to be able in this way to produce a finer spectral pattern. For certain fields of application the light source may also be in the form of an intensity-controllable laser, optionally a multiplicity of lasers being used, as a result of which light distributors and spectral band filters are then unnecessary. A wide band light source with spectral band filter and/or intensity modules connected in tandem may also be combined with an intensity-controlled laser, which renders possible a combined treatment of tissues, if this is considered to be beneficial, in which case a highly versatile device is additionally obtained. In order that the light being introduced via the beam couplers be transmitted to the beam coupler in a suitably prepared form, a light integrator can be connected in tandem to the spectral band filters and/or intensity modules or to the intensity-controlled laser, the light integrator being shared by all the units in the case of combined constructions. Here the exit from the light integrator can be connected directly to the entry to the beam coupler.

To render possible an accurate acquisition of data, the sensors can be designed for the separate detection of the spectral patterns and/or the separate acquisition of electrophysiolocical and/or physiological chemical data, by means or which each signal is separately recorded and is also processable in this form. For the determination of the spectral patterns, the sensor may have monochromators and/or, optionally controllable, filters and/or spectral analysers, which renders possible an accurate analysis of the spectral patterns signalled back from the tissue.

For particularly accurate processing of the data determined by the sensors, a data convertor matched to the data to be determined can be connected in tandem to each of the sensors. The data convertor then transmits these data, suitably processed, to the working data bank.

BRIEF DESCRIPTION OF THE DRAWING FIGURES

In the drawing, exemplary embodiments of the subject matter of the invention are shown in the form of block diagrams of the components.

DESCRIPTION OF THE PREFERRED EMBODIMENTS

Figure 1:
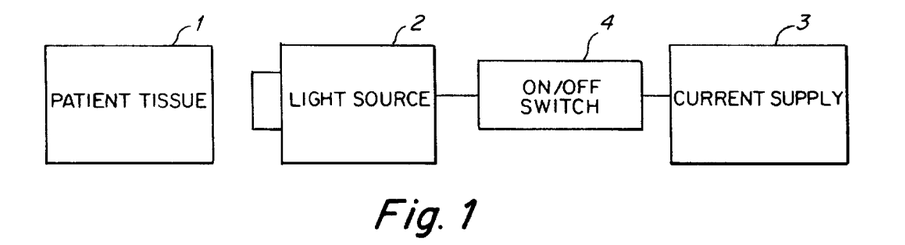
FIG. 1 shows a conventional treatment unit.

In the known design according to FIG. 1, the tissue 1 of the patient is irradiated by a light source 2, which is actuated by a power supply 3. This light source 2 is switchable by an on-and-off switching device 4. It can be seen that the light source is positioned at a distance from the tissue of the patient, so that a rather non-specific radiation impinges on the tissue and considerable losses of radiation to the surroundings cannot be excluded.

Figure 2:
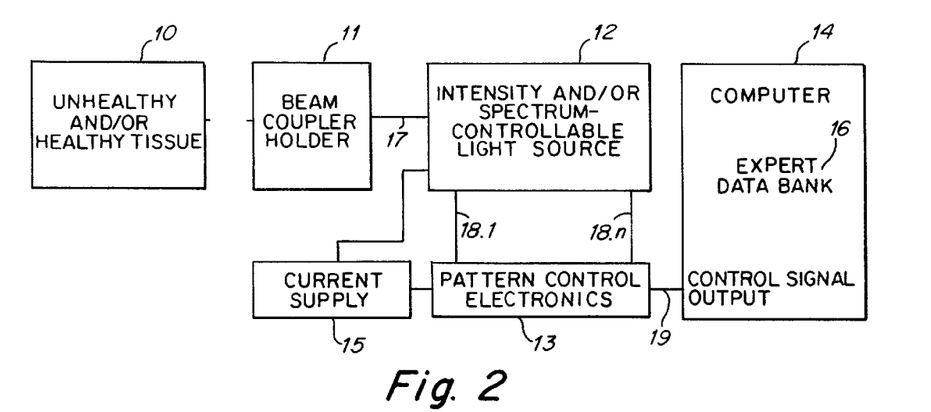
FIG. 2 shows a modified treatment unit, in which the light source is controllable by experimentally determined data.

In a first variant of the design of the device according to the invention, the diseased and/or healthy tissue 10 is exposed via a beam coupler 11 to a light source 12, the intensity and/or spectral pattern of which is controllable. An electronic unit 13 for controlling the pattern, which is addressed via a computer 14, is provided for this control. Both the light source 12 and the electronic unit 13 for controlling the pattern and the computer 14 are supplied by a power supply 15. The commuter contains an expert data bank 16, in which empirically determined data for the treatment of the diseased tissue are stored.

For the operation of the device, the beam coupler 11 is moved up to the diseased tissue in such a way that the field irradiated by the beam coupler coincides with the diseased tissue. The beam coupler receives the light beams or the spectral pattern via the beam output 17 of the light source 12, which is connected via the lines 18.1 to 18.n to the electronic unit 13 for controlling the pattern. The number of lines 18 is determined by the number of bands or spectral ranges by which the light source is actuated. The electronic unit for controlling the pattern receives the appropriate control commands via the control signal output 19 from the computer 14, which extracts the appropriate data from the expert data bank.

Figure 3:
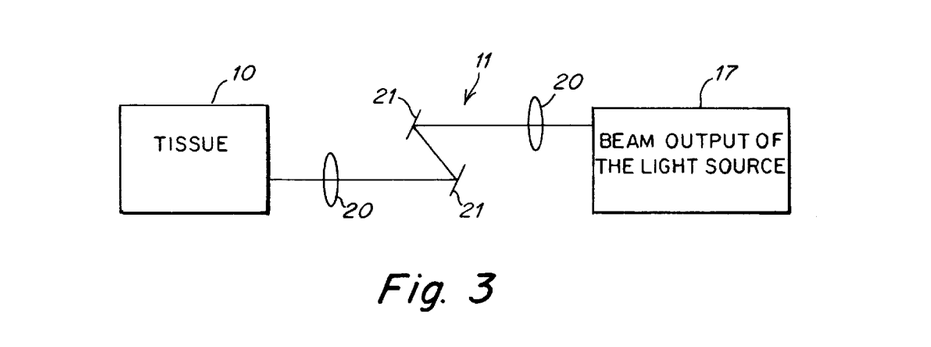
FIG. 3 is a diagram of a first design of a beam coupler having a wide band light source.

In FIGS. 3 to 6, different variants of the beam coupler 11 are shown diagrammatically. FIG. 3 shows a beam coupler constructed from lenses 20 and deviating mirrors 21. An alteration in the pattern emitted by the beam coupler can be effected through the appropriate selection and arrangement of the lenses and the appropriate tilting of the mirrors 21.

Figure 4:
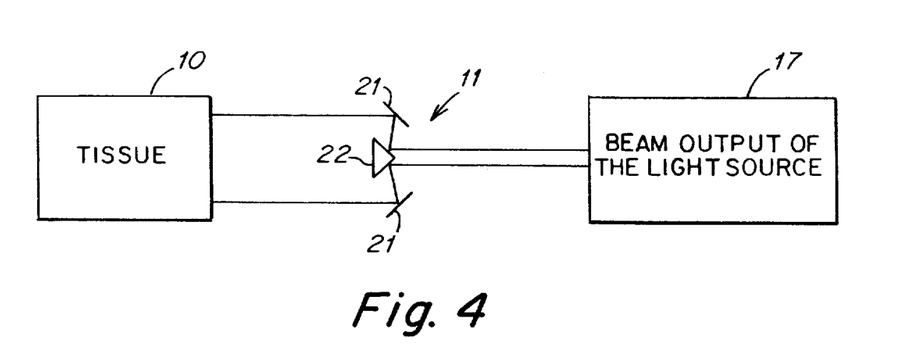
FIG. 4 shows a modified design of the beam coupler for a wide band light source.

In FIG. 4, the beam output 17 impinges on a beam coupler 11, in which the beams of light strike a refractive cone or a refractive prism 22, the reflected beams of light being directed via tilted mirrors 21 to the tissue 10.

Figure 5:
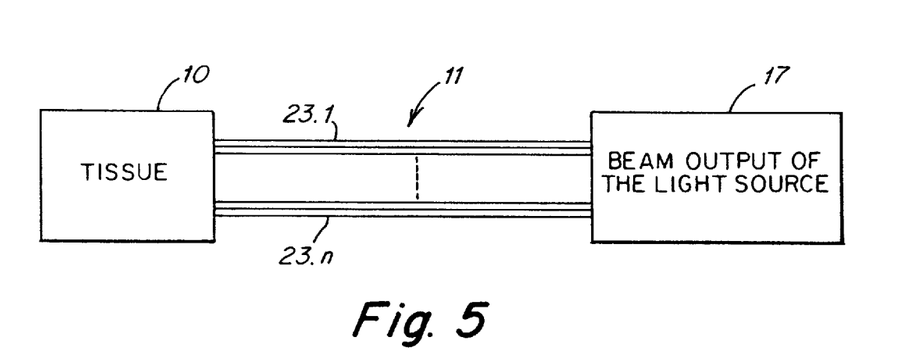
FIG. 5 shows a beam coupler with optical fibres, with a separate fibre being provided for each spectrum.
Figure 6:
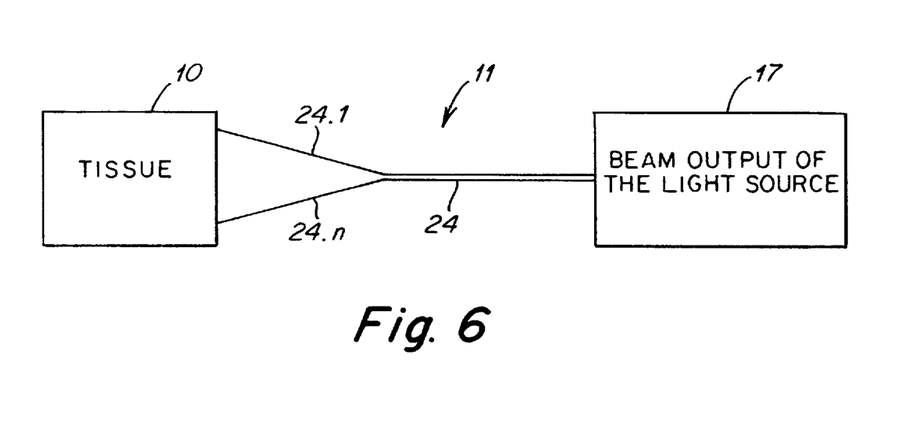
FIG. 6 shows a design similar to that in FIG. 5, in which only one strand of fibre proceeds from the light source and splits up according to the number of spectral bands.

In FIG. 5, the beam coupler is constructed in the form of a bundle of optical fibres, with a given number of optical fibres 23 forming namely the fibres 23.1 to 23.n. Each of these fibres transmits a certain spectral range, so that the combination of optical fibres then emits a given spectral pattern onto the tissue 10. This variant of the design can be modified as shown in FIG. 6 by leading away from the beam output 17 a single bundle of fibres 24, which is divided up on its path into a bundle of fibres 24.1 to 24.n, a definite spectral pattern again being obtainable by this division.

Figure 7:
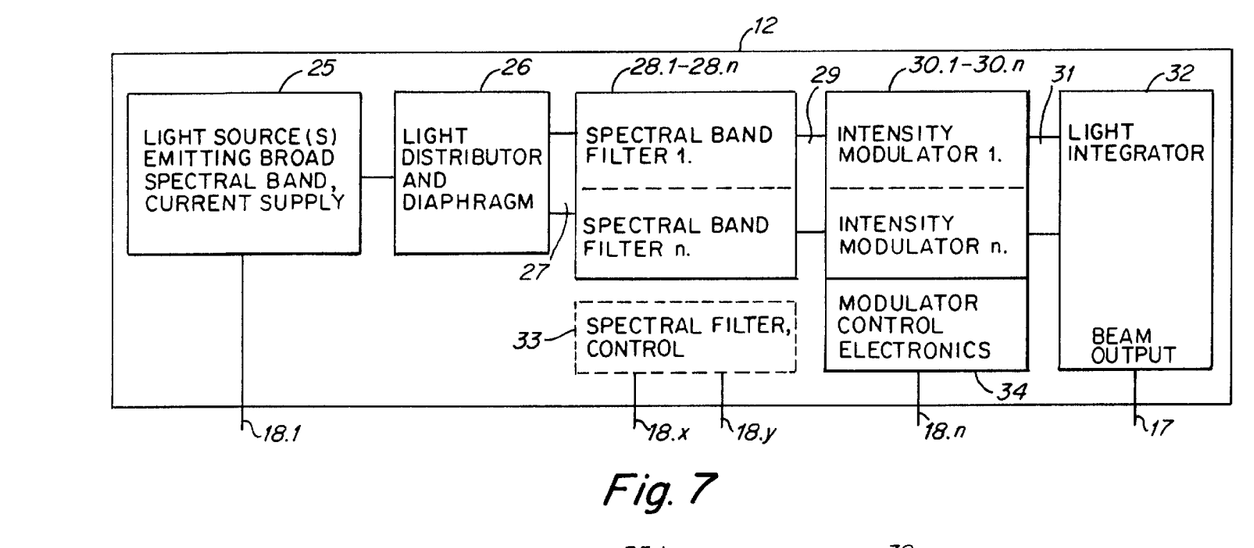
FIG. 7 shows the construction of the controllable light source which has a light source emitting a wide spectral band.

FIG. 7 shows the construction of light source having a controllable intensity and/or spectrum, this light source being acted upon by the electronic unit for controlling the pattern via the lines 18.1 to 18.n. The lines 18.x and 18.y indicated in FIG. 7 are lines from the group 18.1 to 18.n and likewise lead from the electronic unit 13 for controlling the pattern to the respective required section of the light source 12 having a controllable intensity and/or spectrum. This light source possesses a light source 25 which emits a wide spectral band and is connected to a light distributor and/or diaphragm 26. The light issuing from the light distributor and/or diaphragm 26 is further directed via a line 27 past the spectral band filter 28.1 to 28.n and there disperses into a corresponding spectral band pattern. This spectral band pattern is then transmitted via lines 29 to intensity modulators 30.1 to 30.n, which then lead the intensity-modulated beams of light via the line 31 to a light integrator 32. The light entering the light integrator is led via the beam output 17 to the beam coupler and from this is then radiated onto the tissue 10. The spectral band filters 28.1 to 28.n are controllable by a spectral filter 33, which is acted upon by electronic unit for controlling the pattern via the lines 18.x to 18.y. The intensity modulators 30.1 to 30.n are controllable by a corresponding electronic unit 34 for controlling the modulators, which unit is likewise supplied with data from the electronic unit 13 for controlling the pattern via a line 18.n. As already indicated in FIG. 2, this electronic unit 13 for controlling the pattern is supplied with data from the expert data bank 16 via a signal output 19 of the commuter 14.

Figure 8:
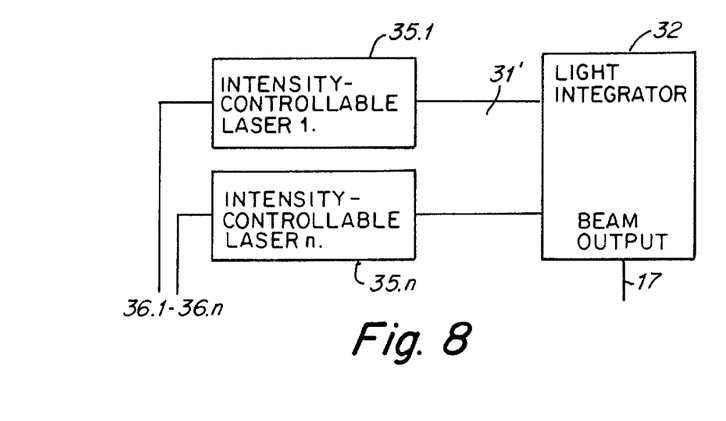
FIG. 8 shows a design similar to that in FIG. 7, but for an intensity-controllable laser.

In FIG. 8, instead of a light source 25 emitting a wide spectral band, the light source provided is at least one intensity-controllable laser 35.1, of which—as may be seen from FIG. 8—there may be an indefinite number up to 35.n. These intensity-controllable lasers are connected via lines 36.1 to 36.n to intensity-controlling devices, via which the lasers can be correspondingly acted upon. The light emerging from the intensity-controllable lasers, which already have a specific spectral band owing to the construction of the laser, is again led via the line 31' to the light integrator 32, which then again acts upon the beam coupler 11 via the beam output 17. Because the intensity-controllable lasers 35.1 to 35.n can be controlled individually, each of the spectral bands can be separately controlled with respect to the intensity and/or time, and this can be effected more simply than in the case of the design in FIG. 7, where the intensity modulators have to be controlled via a special electronic unit 34 for controlling the modulators, the spectral filter control 33 also having to be correspondingly acted upon, that is, in combination with the electronic unit 34 for controlling the modulators.

Figure 9:
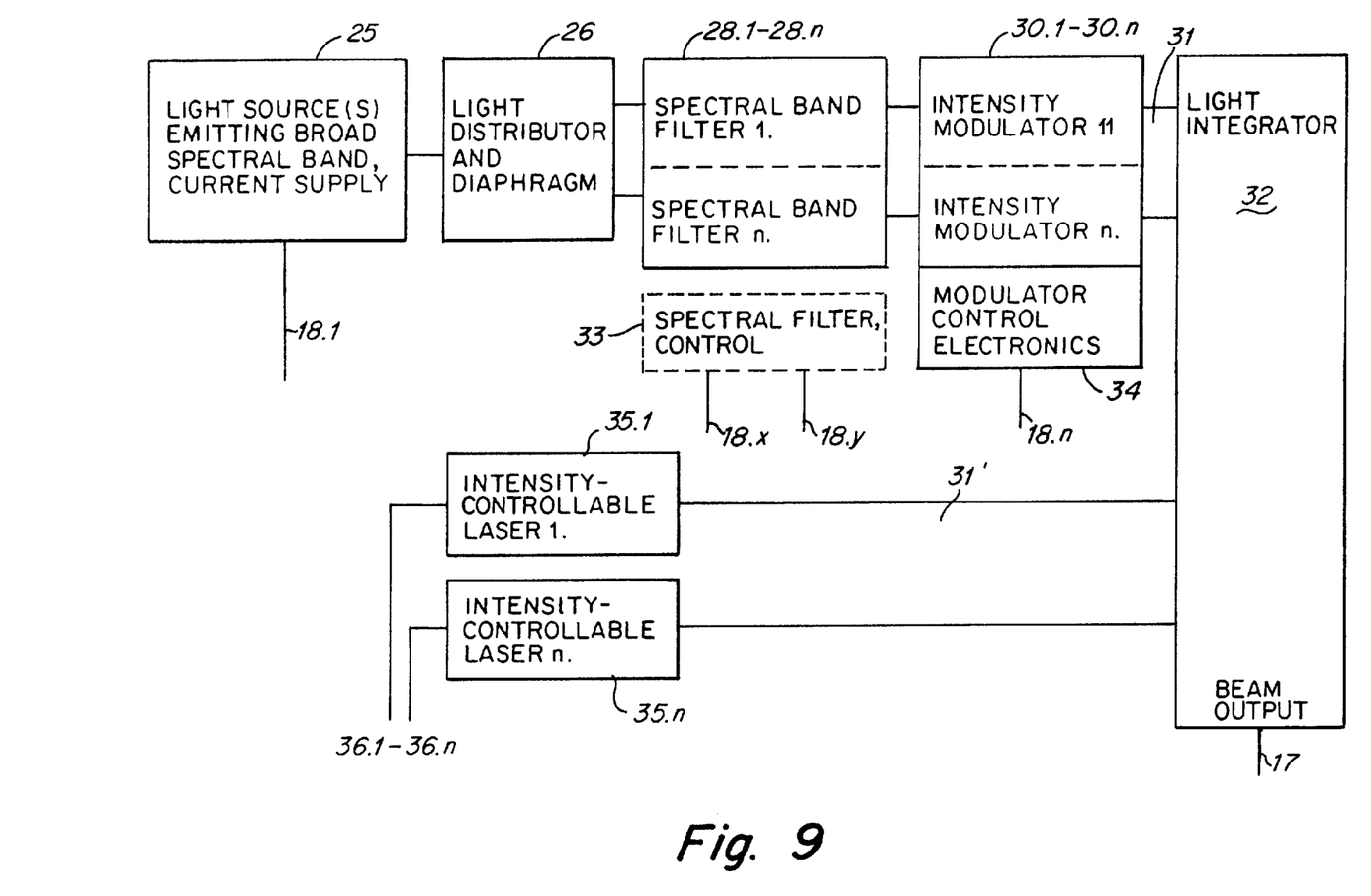
FIG. 9 shows a combined construction having a light source emitting a wide spectral band and several intensity-controllable lasers.

The variant of the design shown in FIG. 9 is a combination of the embodiments in FIGS. 7 and 8, the reference numbers used being the same as in FIGS. 7 and 8. This affords the possibility of attaining an even more precise control of the radiation, as the laser beams can be coordinated as a supplement to the beams coming from the light source emitting the wide spectral band, so that here quite narrow spectral ranges can be intensified in order thus to attain the desired radiation.

Figure 10:
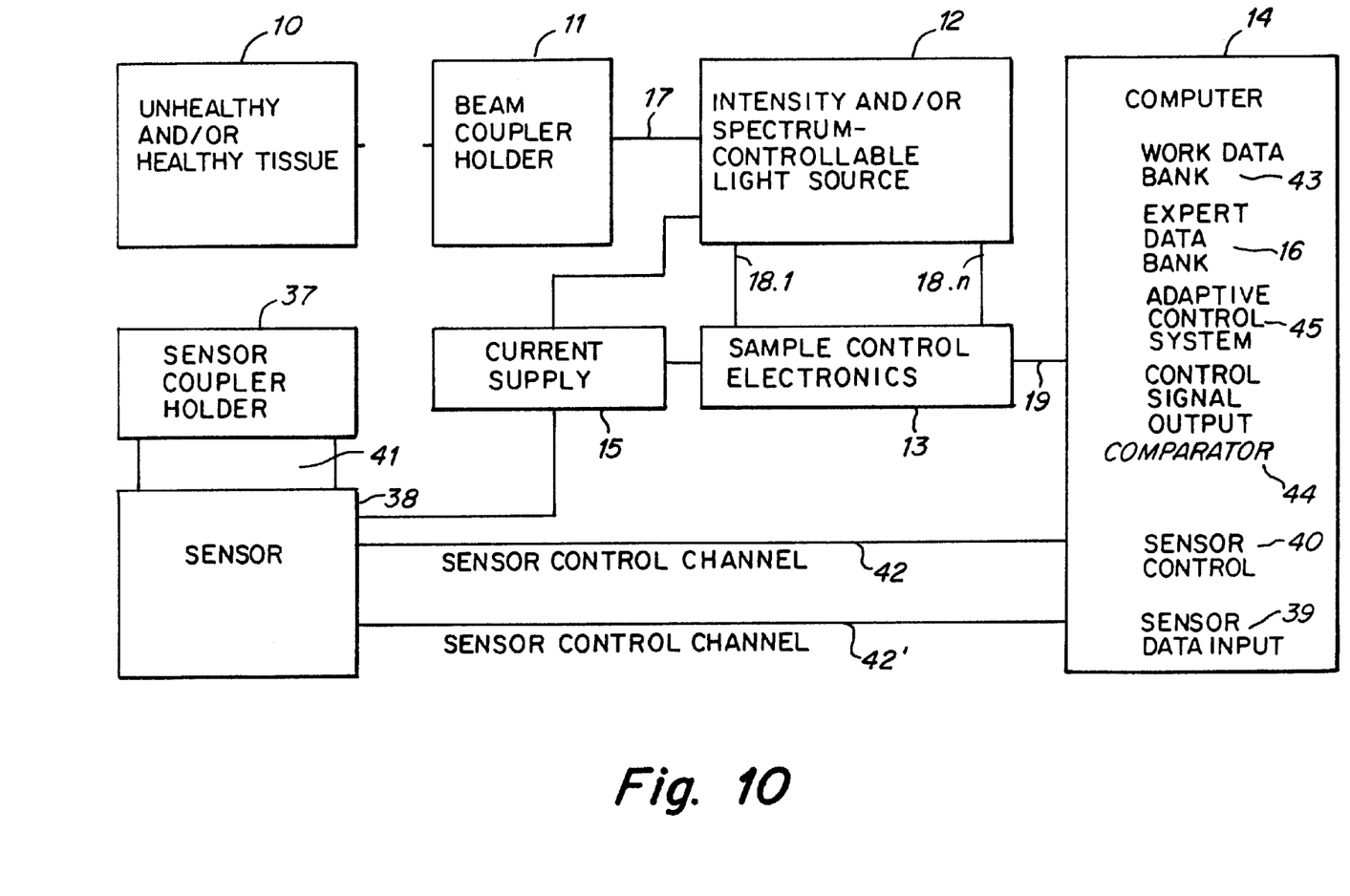
FIG. 10 shows an overall assembly of the device according to the invention, which has in addition to the radiation unit a sensor unit for the determination of the tissue data.

The variant of the design according to FIG. 10 has as its radiation unit the embodiment already described in FIG. 2, but with the additional provision of a data acquisition unit consisting of a sensor coupler 37, a sensor 38, a sensor data input 39 and a sensor control 40. The sensor coupler 37 is connected via corresponding lines 41 to the sensors 38 and a corresponding sensor control channel 42 and a sensor data channel 42' lead to the sensor control. Within the computer 14, in addition to the sensor control 40 and the sensor data input 39, there are also provided a working data bank 43, a comparator 44 and an adaptive control system 45.

In this embodiment, light coming from the light source 12 via the beam coupler is emitted into diseased and/or healthy tissue in accordance with the values from the expert data bank 16 via the commuter 14. At the same time, the reaction of the tissue to the emitted light is determined via the sensor coupler 37, the line 41 and the sensor 38, the corresponding sensor data being supplied to the computer 14 via the sensor data channel 42' and the sensor data input 39. This computer then processes the data from the sensor data input via the working data bank 43 and the comparator 44 and the latter compares the data determined via the sensor data input 39 with that of the expert data bank 16. These comparative data can be analysed via the adaptive control system 45 and it can be determined whether the tissue yields values closer to or more remote from those of the expert data bank. The direction of the reaction is thereby determined via the adaptive control system and, depending on the value and trend determined, the sensor control 40 and the electronic unit for controlling the pattern are acted upon appropriately, so that the electronic unit 13 for controlling the pattern then adjusts the light source 12 having a controllable intensity and/or spectrum, in such a way that the required direction of the reaction is achieved. In the same way, the sensor also is appropriately readjusted via the sensor control 40, in order thus for the sensor to be ready to receive the amended data.

Figure 11:
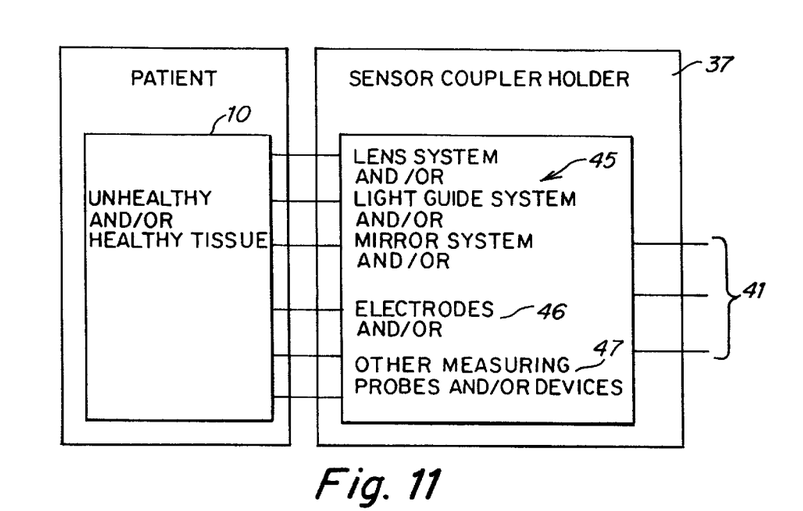
FIG. 11 shows the construction of a sensor coupler and the connection with the tissue.

Here the construction of the sensor coupler 37 can be similar to that of the beam coupler 11, a lens system and/or an optical fibre system and/or a mirror system or a combination of these systems possibly being provided in this sensor coupler. These designs correspond approximately to the construction shown in FIGS. 3 to 6. This lens system and/or an optical fibre system and/or a mirror system is indicated in FIG. 11 by the number 45.

In addition to this pure light control system, there may also be electrodes 46 and other sensing probes 47, by means of which electrical potentials, oxygen saturation or other physical and/or physiological chemical measured data can be obtained. The electrodes 46 may be surface electrodes and/or probe electrodes and/or microelectrodes, which can deduct and record potential differences present in the tissue. The other sensing probes can be used for recording the concentration of many different kinds of substances, such as oxygen gases, solid and liquid substances, and geometric positions, volumes, masses and vibrations. There may also be chemical parameters, such as tissue impedance, NADH, MPA, lactic acid probes, tissue sensing probes or blood sugar sensing probes, blood circulation sensing probes, temperature sensing probes et cetera, as all these data indicate the reaction of the cell to the radiation. In this connection, in particular the combined measurements of oxygen, temperature and lactic acid have proved to be especially useful.

Figure 12:
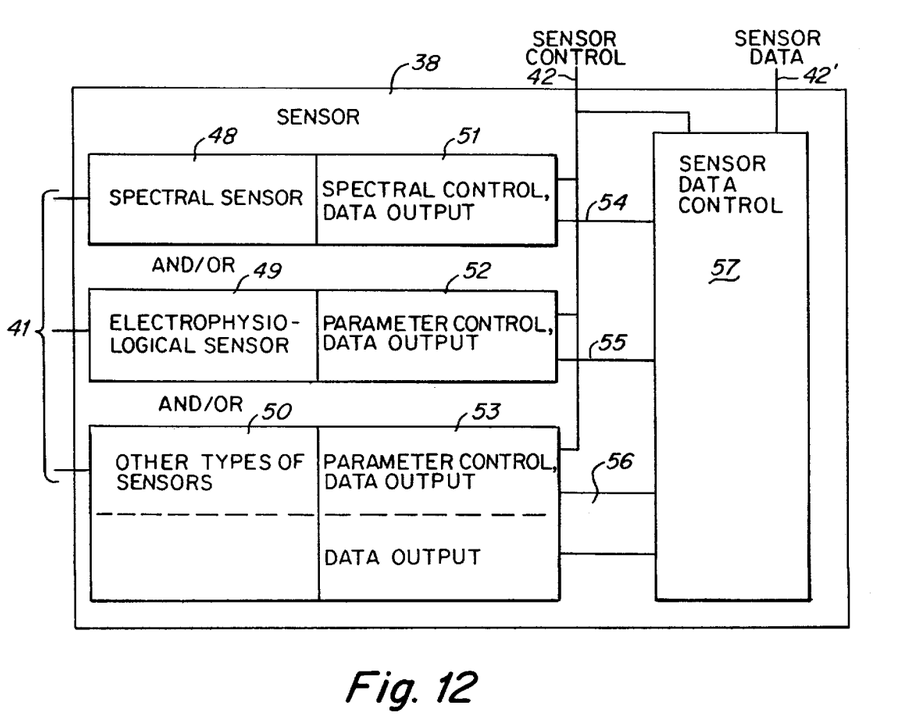
FIG. 12 is a diagram of the construction of the sensor.

FIG. 12 shows the analysis in the sensor 38, the measurements of the spectral analysis being recorded via the line 41 in the spectral sensor 48, the chemical physiological and electrophysiological data being recorded in the sensor 49 and the other sensor data being recorded in the sensor 50. To each of these sensors is serially connected a special control 51, 52 and 53, which are acted upon via the lines 54, 55 and 56 by the sensor data control 57, which is acted upon by the sensor control 42. The sensor data are withdrawn from the data output of the spectral control 51, and from the variable control 52 or 53 and also admitted to the sensor data control 57, which then transmits the sensor data via the line 43 to the sensor data input 39 of the computer 14.

Figure 13:
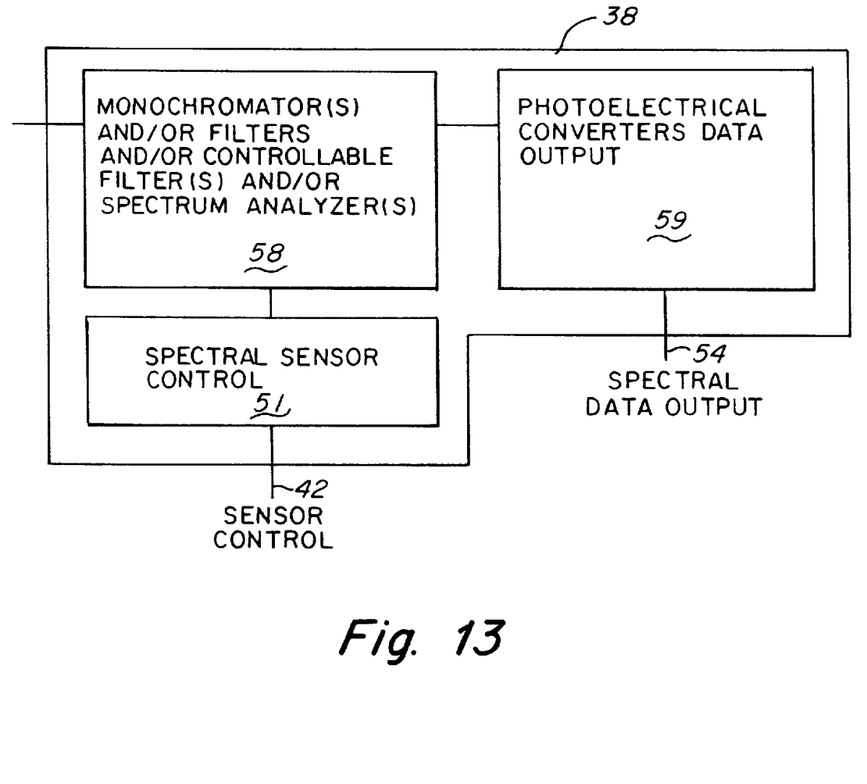
FIG. 13 reproduces the spectral sensor in greater detail.

In the details of the spectral sensor 48 shown in FIG. 13, monochromators and/or filters or controllable filters and/or spectral analysers 58 are provided, which are acted upon by the spectral sensor control 51, which for its part gets the commands from the sensor control 40, again via the line 42. The data determined by the monochromators and/or filters and/or controllable filters or spectral analysers 58 are transmitted via a photoelectric convertor 59 and the corresponding data output 54 to the sensor data control 57.

The design according to FIG. 10 can be controlled in such a way that the data transmitted via the sensor coupler 37, the sensors 38 and the sensor data channel 42' to the computer 14 are those which are read from a healthy section of tissue. These data are then entered into the expert data bank 16 as so-called desired values and the tissue is irradiated via the light source 12 and the beam coupler 10, the reaction of the tissue again being determined via sensors. The desired values in the expert data bank, which have been determined from the healthy tissue, are then compared in the comparator 44 with the data determined by the sensors from the diseased tissue after irradiation and are analysed via the working data bank, the adaptive control system 45 again analysing the direction of the reaction.

Figure 14:
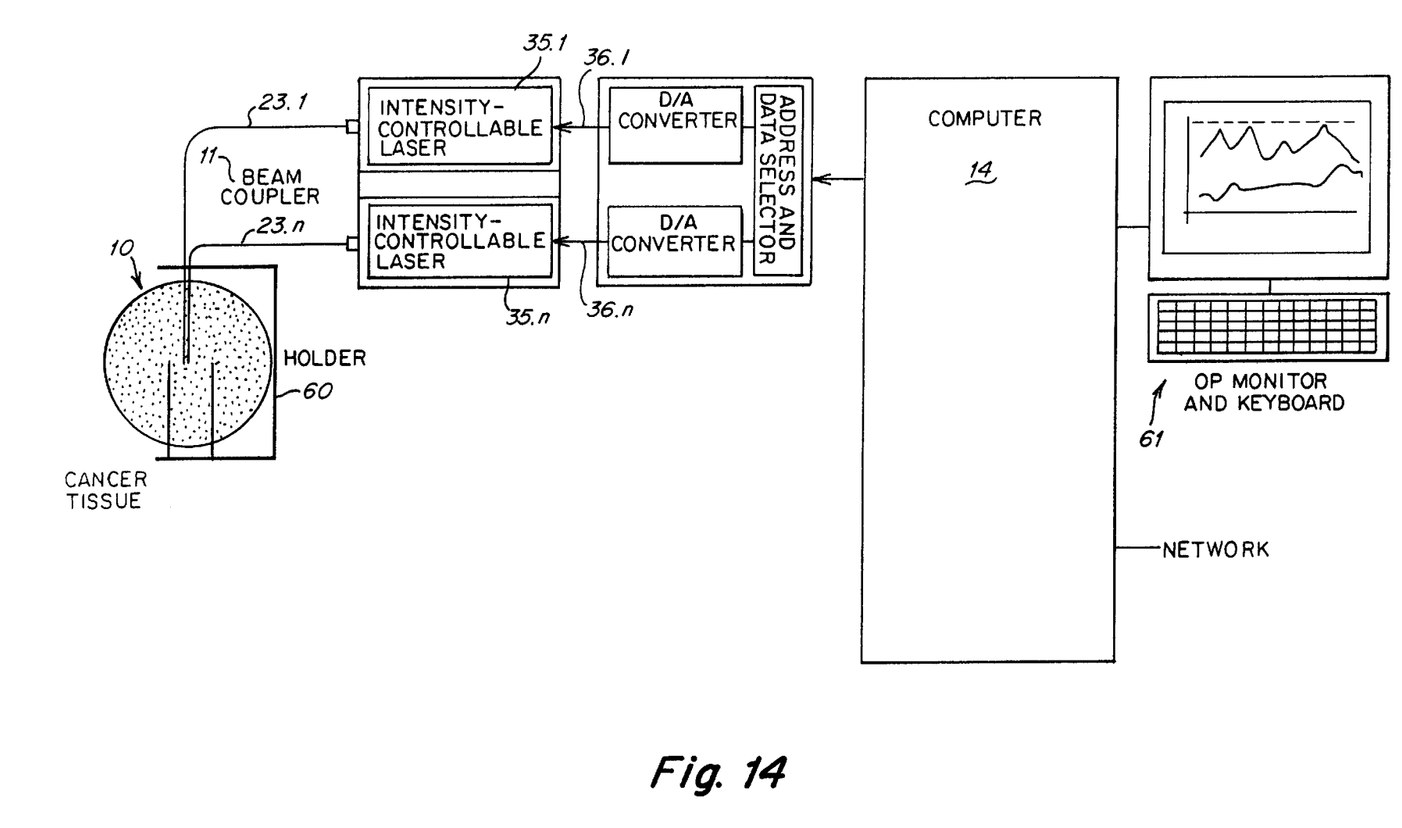
FIG. 14 illustrates an overall design of the device according to the invention with intensity-controllable lasers, in which the control is effected by means of an exert data bank without feedback information from the tissue.

The variant of the design shown in FIG. 14 shows a radiation device similar to that in FIG. 2, that is, a device equipped with intensity-controllable lasers 35.1 to 35.n, the lasers being acted upon via lines 36.1 to 36.n by the computer 14 via D/A convertors and an address and data separator. The digit 60 indicates a holder for the beam coupler, provided for the purpose of direction onto the tissue 10. The input and monitoring unit is indicated generally by 61.

Figure 15:
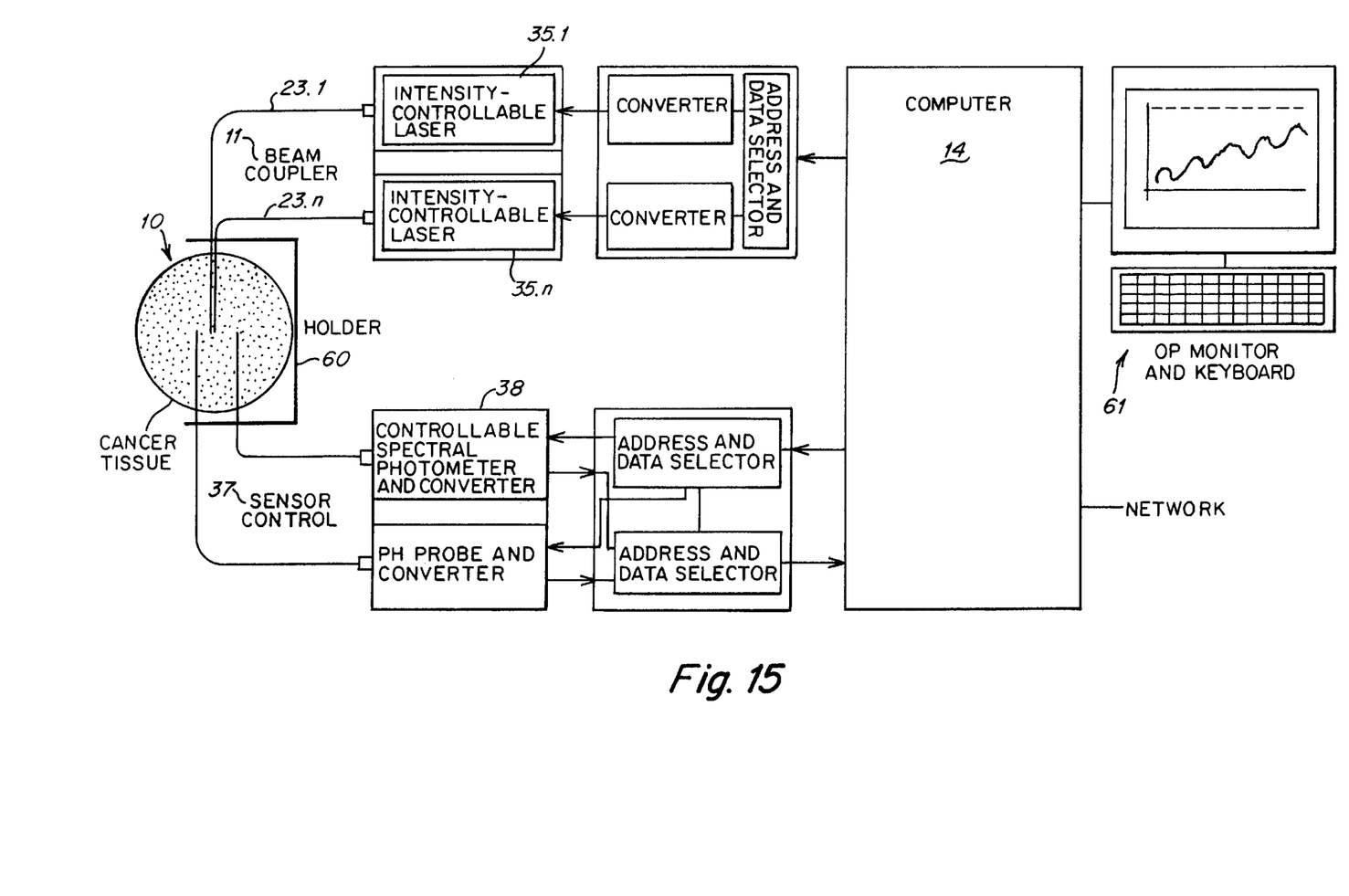
FIG. 15 shows a design similar to FIG. 14, which possesses in addition sensor couplers and sensors for determining tissue data altered by the irradiation.

The device shown in FIG. 15 corresponds to the device represented in FIG. 10, the radiation device again being formed by intensity-controllable lasers. The sensor 38 here has a controllable spectral photometer and a pH probe, which each have a D/A convertor and are connected to the computer via an address and data selector. The radiation unit of the arrangement corresponds to that in FIG. 14.

FIG. 1

1—patient tissue, 2—light source, 3—current supply, 4—on/off switch

FIG. 2

10—unhealthy and/or healthy tissue, 11—beam coupler holder, 12—intensity and/or spectrum-controllable light source, 13—pattern control electronics, 14—COMPUTER, 15—current supply, 16—expert data bank, 19—control signal output

FIG. 3

10—tissue, 17—beam output of the light source

What is claimed is:

1. A device for the photodynamic treatment of living beings and of organs thereof respectively, comprising:

a light source being controllable with regard to its intensity, time, wavelength and spectral bands respectively;

a switching device;

a power source; and means for detecting the reaction of the treated living being and the organs thereof respectively;

wherein for adapting the device for use for an adaptive treatment tailored to the treated patient by data signaled back, which treatment is based on cooperating with biophotochemical effects initiating colors and on tissue-photons-interactions, a computer (14) is provided having an expert data bank (16) and a working data bank (43) as well as a comparator (44), said computer (14) is connected to the light source (12) and to sensors (38) for detecting the reaction of the cancerous cells of the treated living being or tissue or organ respectively suffering under cancer by detecting data of the cancerous cells showing their reaction, said data being selected from the group of oxygen concentration, tissue impedance, volume, blood circulation, NADH and MPA-concentration or temperature respectively; and wherein by an adaptive control system (45) and by the comparator (44) under comparing the sensor data with the data stored in the expert data bank the found compared data are evaluated and whereafter the computer (14) controls the light source (12) in dependence on the evaluation of the compared data.

2. Device in accordance with claim 1, wherein a beam coupler (11) for targeted application of light radiation into the tissue is connected in front of the light source (12).

3. Device in accordance with claim 2, wherein the beam coupler (11) has a lens (21) and/or mirror system (21) for directing and/or selecting the light radiation.

4. Device in accordance with claim 3, wherein a reflection prism or cone (22) is inserted into the beam path in the beam coupler (11) for aligning and/or selecting the light radiation.

5. Device in accordance with claim 2, wherein the beam coupler (11) has a light guide lens (23.1–23.n, 24, 24.1–24.n) for aligning and/or selecting the light radiation.

6. Device in accordance with claim 2, wherein the devices provided in the beam coupler, for aligning and/or selecting the light radiation are adjustable to one another for the geometrical shape of the surface to be irradiated.

7. Device in accordance with claim 2, wherein sensor couplers (37) for targeted determination of the data of the tissue to be treated are connected in front of the sensors (38).

8. Device in accordance with claim 7, wherein the sensor couplers (37) are designed analogous to the beam couplers (11).

9. Device in accordance with claim 7, wherein the sensor coupler (37) also contains electrodes (46) and/or measuring probes (47) for additional determination of physical and/or physiological-chemical measurement data, in addition to the lens and/or minor and/or fiberoptic systems (45).

10. Device in accordance with claim 2, wherein each individual component can be controlled separately in the case of several spectral band filters (28.1–28.n) and/or intensity modules (30.1–30.n) connected behind a broad band light source (25).

11. Device in accordance with claim 10, wherein a light integrator (32) is connected to the spectral band filter (28.1–28.n) and/or intensity modules (30.1–30.n) or the intensity-controlled laser(s) (35.1–35.n), the light integrator (32) being common for all units in case of combined designs.

12. Device in accordance with claim 11, wherein the output (17) of the light integrator is connected directly with the input (17) of the beam coupler (11).

13. Device in accordance with claim 1, wherein a broad band light source (25) with spectral band filters (28.1–28.n) and/or intensity modules (30.1–30.n) is combined with one or more intensity-controlled laser(s) (35.1–35.n).

14. Device in accordance with claim 1, wherein the sensors (38) are designed for separate determination of the spectral pattern and/or electro-physiological and/or physiological-chemical data.

15. Device in accordance with claim 14, wherein the sensor (38) for determining the spectral pattern has monochromators and/or, in a given case, controllable filters and/or spectral analyzers (58).

16. Device in accordance with claim 14, wherein a data converter matched with the data to be determined is connected to each of the sensors (38).

* * * * *